United States Patent [19]

Celmer et al.

[11] 3,991,183
[45] Nov. 9, 1976

[54] ANTIBIOTIC PRODUCED BY A SPECIES OF MICROMONOSPORA

[75] Inventors: Walter D. Celmer, New London; Walter P. Cullen, East Lyme; Charles E. Moppett, Mystic; John R. Oscarson, Groton; John B. Routien, Lyme, all of Conn.; Riichiro Shibakawa; Junsuke Tone, both of Aichi, Japan

[73] Assignee: Pfizer Inc., New York, N.Y.

[22] Filed: May 1, 1975

[21] Appl. No.: 573,546

[52] U.S. Cl. .................................... 424/118
[51] Int. Cl.² ................................ A61K 35/00
[58] Field of Search ........................... 424/118

[56] References Cited

UNITED STATES PATENTS

| 3,091,572 | 5/1963 | Luedemann et al. ............... 424/118 |
| 3,454,696 | 7/1969 | Weinstein et al. ................. 424/118 |
| 3,499,078 | 3/1970 | Luedemann et al. ............... 424/118 |

*Primary Examiner*—Albert T. Meyers
*Assistant Examiner*—Daren M. Stephens
*Attorney, Agent, or Firm*—Connolly and Hutz

[57] ABSTRACT

Antibiotic Compound 37,504 is produced by the submerged aerobic fermentation under controlled conditions of a new species of Micromonospora designated *Micromonospora viridifaciens* sp. nov. Routien, ATCC 31146.

3 Claims, 1 Drawing Figure

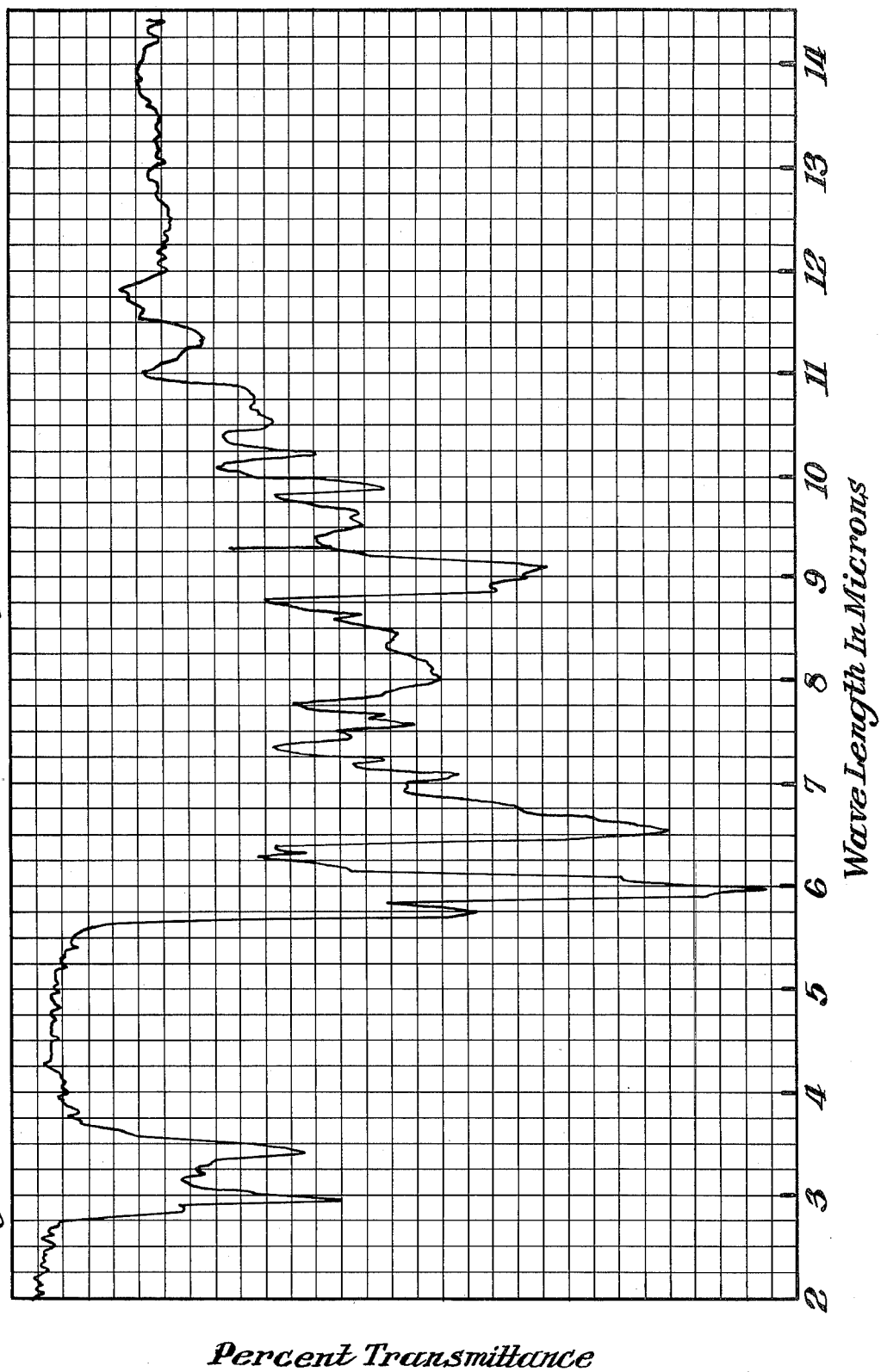

ANTIBIOTIC PRODUCED BY A SPECIES OF MICROMONOSPORA

BACKGROUND OF THE INVENTION

The search for new antibiotics produced by soil microorganisms has encompassed the screening of various genera of bacteria, higher bacteria and fungi including many species within each genus and many strains within each species.

Microorganisms that have received relatively little attention include the genus Micromonospora, a genus closely resembling Streptomyces but differing in the lack of aerial mycelium and with very narrow hyphae on which minute spores are borne singly. Media used for the growth and identification of members of this genus are described by M. J. Weinstein et al. in Antimicrobial Agents and Chemotherapy 435–437 (1967/1968).

SUMMARY OF THE INVENTION

This invention is concerned with Compound 37,504, a new antibiotic produced under submerged aerobic fermentation conditions by *Micromonospora viridifaciens* sp. nov. Routien, ATCC 31146. Methods for its recovery and purification are described and some of its antimicrobial properties are outlined.

DETAILED DESCRIPTION OF THE INVENTION

The microorganism useful for the preparation of the antibiotic of this invention was isolated from a soil sample from Japan. This culture (Pfizer F.D. 23988), designated *Micromonospora viridifaciens* sp. nov. Routien, has been deposited in the American Type Culture Collection, Rockville, Md. under their accession number ATCC 31146. The permanency of the deposit and ready accessibility thereto by the public are afforded in the event the patent is granted. Access to the culture is available during pendency of the application under Rule 14 and 35 USC 112. All restrictions on the availability to the public of the culture deposited will be irrevocably removed upon granting of the patent.

The culture was planted in two to six slants or Petri dishes of media and incubated at 28° C. unless otherwise noted. Readings were taken at various times, but most recordings of growth were after 14 days of incubation.

The media and references to their composition are as follows:

1. Emerson's Agar (and 0.1% CaCO₃) — Waksman, S. A., *The Actinomycetes*, Vol. 2, 1961. Medium 28 on p. 331.
2. Glucose Yeast Extract Agar (and 0.1% CaCO₃). M. J. Weinstein et al., *Antimicrobial Agents and Chemotherapy*, 1967: 435–437. 1968.
3. Glucose Asparagine Agar (and 0.1% CaCO₃). Waksman, 1961. Medium 2 on p. 328.
4. Czapek — Sucrose Agar (and 0.1% CaCO₃). Waksman, 1961. Medium 1 on p. 328.
5. Gelatin (and 0.1% CaCO₃). Waksman, 1961. Medium 20 on p. 330.
6. Starch (and 0.1% CaCO₃). Waksman, 1961. Medium 21 on p. 330.
7. Tyrosine Agar. R. E. Gordon and M. M. Smith, *Jr. Bact.* 73: 15–27. 1957.
8. Potato-Slices. G. M. Luedemann and B. C. Brodsky, *Antimicrobial Agents and Chemotherapy* — 1964: 47–52. 1965.
9. Potato-Slices (and CaCO₃). Luedemann and Brodsky op. cit.
10. Glucose-Nitrate Broth. Waksman, *The Actinomycetes*, 1950. p. 193.
11. Organic Nitrate Broth. Waksman, 1961. Medium 37 on p. 332.
12. Cellulose. M. Levine and H. W. Schoenlein, *A Compilation of Culture Media*, 1930. Medium 2511 on p. 823.
13. Cellulose. H. L. Jensen, *Proc. Linnean Soc. N. S. Wales*, 55:231–248. 1930.
14. Peptone Iron Agar with Lead Acetate Strips. Waksman, 1961. Medium 38 on p. 332.
15. Difco Skim Milk.
16. Sucrose Inversion. Levine and Schoenlein, 1930. Medium 622 on p. 176.
17. ATCC Medium No. 172 for Temperature Range. ATCC Catalog of Strains, 9th edition, p. 172. 1970.
18. Nitrogen Utilization. Weinstein et al. p. 437. 1968.
19. Carbohydrate Utilization. Weinstein et al. p. 437. 1968.

In the following description the colors of the mycelium are designated by both a personal, descriptive term and by reference to an appropriate color chip from the *Color Harmony Manual*, 4th edition, 1958, published by the Container Corporation of America.

Emerson's Agar plus CaCO₃ — growth good, roughened; color orange (near 3 nc to 3 pe one time and near 4 pa to 4 la another) with olive-colored areas; soluble pigment yellow brown, sometimes with greenish tinge near end of streak; fetid odor.

Glucose Yeast Extract Agar plus CaCO₃ — growth good, flat, ridged; color light orange often with olive cast (near 3 lc to 3 le one time and near 4 ia another); pale yellowish-green soluble pigment; fetid odor.

Glucose Asparagine Agar plus CaCO₃ — growth very poor; colorless; no soluble pigment; no odor.

Czapek-Sucrose Agar — growth poor, flat; colorless to pale orange (near 4 ca); no soluble pigment; no odor.

Potato Slice — growth moderate to good, wrinkled; color orange (4 pe to 5 pe); brown soluble pigment; slight fetid odor.

Potato Slice plus CaCO₃ — growth moderate to good, wrinkled, thin; color orange (near 4 pe to 5 pe); brown soluble pigment; fetid odor.

Tyrosine Agar — growth very poor; colorless to near 2 gc; very pale tan to brown soluble pigment; no odor.

Biochemical Properties — nitrates not reduced in either medium even after twenty one days; gelatin liquefied; hydrogen sulfide weakly produced (very poor growth); tyrosine not digested; milk coagulated and peptonized slowly (21 days); sucrose inversion; no growth on cellulose strips in either medium even after forty two days; melanin not produced; growth from 21°–45° C. with best growth from 28°–45° C.; yeast extract and NZ Amine A utilized as nitrogen sources, but sodium nitrate, asparagine and glutamic acid not utilized; carbohydrate utilization pattern, based on tests over a period of months, showed d(−) ribose and starch always utilized and adonitol, L-arabinose, inositol, lactose, D-mannitol, D-mannose, D-melibiose, raffinose, rhamnose and sorbitol never utilized; positive results with glucose, sucrose, xylose and trehalose, and variable results with dulcitol, galactose and levulose. The variations in results were not due to technique but probably to some unknown and uncontrollable factors.

Spores — only on substrate mycelium. On glucose yeast extract agar plus calcium carbonate spores scattered or in loose aggregations or in clusters, mostly stalked, mostly slightly elliptical, $1.0 \times 0.8~\mu$, but sometimes round, 0.6 to 1.0 $\mu$ wide, surface covered with stout, short pointed projections as revealed by scanning electron microscope.

The culture could not be identified as any described species and was therefore designated as a new species. Because of the greenish tinge that developed on a number of solid and liquid media, it was named *Micromonospora viridifaciens* sp. nov. Routien.

Cultivation of *M. viridifaciens* preferably takes place in aqueous nutrient media at a temperature of about 28°–36° C., and under aerobic, submerged conditions with agitation. Nutrient media which are useful for such purposes include a source of assimilable carbon such as sugars, starch, glycerol and molasses; a source of organic nitrogen such as fish meal, casein, enzymatic digest of casein, meat meal, wheat gluten, cottonseed meal, soybean meal and peanut meal. A source of growth substances such as distillers' solubles and/or yeast extract as well as salts such as sodium chloride, ammonium acetate, ammonium sulfate, potassium phosphate and trace minerals such as iron, magnesium, zinc, cobalt and manganese may also be utilized with advantageous results. If excessive foaming is encountered during fermentation, antifoam agents such as vegetable oils or silicones may be added to the fermentation medium. The pH of the fermentation tends to remain rather constant but if variations are encountered, a buffering agent such as calcium carbonate may also be added to the medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the microorganism and throughout its growth.

Inoculum for the preparation of the antibiotic may be obtained by employing growth from slants or Roux bottles of *M. viridifaciens* on such media as ATCC Medium 172 to which previous reference was made. The growth may be used to inoculate either shake flasks or inoculum tanks, or alternatively, the inoculum tanks may be seeded from the shake flasks. The growth of the microorganism usually reaches its maximum in about two or three days. However, variations in the equipment used, aeration, rate of stirring, etc. may affect the speed with which the maximum growth is reached. In general, the fermentation is conducted until substantial antimicrobial activity is imparted to the medium, a period of from about 24 hours to about 4 days being sufficient for most purposes.

The process of antibiotic production is conveniently followed during fermentation by biological assay of the broth employing a sensitive strain of *Staphylococcus aureus*. Standard plate assay technique is employed in which the zone of inhibition surrounding a filter paper disc saturated with the broth is used as a measure of antibiotic potency. After the fermentation broth has reached a desired level of antibiotic potency, the pH is usually about 7.5–8.5, the mycelium is removed by filtration or centrifugation.

Thin layer chromatography employing silica gel is a useful tool for analyzing the antibiotic(s) produced by *M. viridifaciens* in fermentation media and the composition of crude and purified materials extracted from fermentation broths. The developing system is chloroform:methanol (3:1 v/v). Antibiotic Compound 37,504 is a pale yellow material which may be observed visually at high concentrations. Lower concentrations of Compound 37,504 and small amounts of more polar antibiotics which may be present are conveniently visualized by exposure of the developed silica gel chromatograms to 366 mu light where the antibiotics show up as brilliant fluorescent spots under these conditions. Bioautographic detection of the antibiotic components may be accomplished by means of an overlay of a thin layer of agar seeded with a sensitive strain of *Staphylococcus aureus* or other sensitive organism on the developed silica gel chromatograms.

Compound 37,504 may be recovered from fermentation broth by a number of different procedures including solvent extraction and column chromatography or combinations thereof. Various organic solvents are useful in extracting the antibiotic from clarified fermentation broth, or more conviently on a large scale, from whole (unfiltered) fermentation broth. Solvents such as butanol, methyl isobutyl ketone, ethyl acetate, chlorinated hydrocarbons, benzene and isopropyl ether may be used at pH ranges from 4.0 to 10.0, preferably 7.0.

The preferred method of separation and recovery of Compound 37,504 is as follows: Whole fermentation broth adjusted to pH 7.0 is twice extracted with ⅓ to ½ volumes of methyl isobutyl ketone. The solvent extract is concentrated under vacuum and the antibiotic precipitated by addition of three volumes of heptane. The material that separates is collected by filtration and dried in vacuo. The dried material dissolved in chloroform is applied to a column of silica gel $PF_{254}$ made up in chloroform. The column is developed under 80 psi with chloroform, chloroform:methanol (98:2% v/v) and chloroform:methanol (95:5% v/v). Column cuts containing desired Compound 37,504, located by thin layer chromatography, are taken to dryness under vacuum. The amorphous yellow powder is treated with activated charcoal in chloroform: methanol solution (1:1 v/v) and again taken to dryness.

The present invention includes within its scope the dilute forms and crude concentrates of Compound 37,504 and the purified antibiotic. All of these products are useful in combatting microorganisms, especially *Mycobacterium tuberculosis*, *Diplococcus pneumoniae*, *Streptococcus pyogenes* and *Staphylococcus aureus*. In addition they are useful as disinfectants against such microorganisms and as an aid in the purification of mixed cultures for medical and diagnostic and biological research purposes.

Table I illustrates the antibiotic spectrum of Compound 37,504. These tests were run by preparing tubes of nutrient broth with gradually increasing concentrations of the pure antibiotic and then seeding the broths with the particular organisms specified. The minimal inhibitory concentration indicated in Table I is the minimal concentration of the antibiotic (in micrograms/ml) at which the microorganism failed to grow. The tests were conducted under standardized conditions as described in Proc. Soc. Exp. Biol. & Med., 122, 1107 (1966). Mice experimentally infected with *Staphylococcus aureus* are protected by the oral or subcutaneous administration of Compound 37,504 at about 200 mg/kg.

Table I

| Organism | CP-37,504 |
|---|---|
| *Staph. aureus* | |
| 01A005 | < .10 |
| 01A052 | < .10 |
| 01A109 | < .10 |
| 01A110 | < .10 |
| 01A111 | < .10 |
| 01A087 | < .10 |
| 01A400 | < .10 |
| *Strep. faecalis* | |
| 02A006 | < .10 |
| *Strep. pyogenes* | |
| 02C203 | < .10 |
| *Mycobact. smegatis* | |
| 05A001 | .78 |
| *B. subtilis* | |
| 06A001 | < .10 |
| *E. coli* | |
| 51A229 | > 200 |
| 51A266 | > 200 |
| 51A125 | > 200 |
| *Ps. aeruginosa* | |
| 52A104 | > 200 |
| 52A440 | > 200 |
| *Klebsiella pneumoniae* | |
| 53A009 | > 200 |
| 53A031 | > 200 |
| *Proteus mirabilis* | |
| 57C064 | > 200 |
| *Proteus morganii* | |
| 57G001 | > 200 |
| *Salm. cholerae-suis* | |
| 58B242 | > 200 |
| *Salm. typhimurium* | |
| 58D009 | > 200 |
| 58D013-C | > 200 |
| *Past. multocida* | |
| 59A001 | < .10 |

The antibiotic of this invention can be administered via the oral or parenteral routes for the treatment in animals, including humans, of pneumococcal, streptococcal, staphylococcal, tubercular and other antibiotic-sensitive infections. In general, these antibiotics are most desirably administered in daily oral doses of 0.5–1 gram or parenteral injections of 100 to 500 mg., depending on the type and severity of the infection and weight of the subject being treated.

The compounds of this invention may be administered alone or in combination with pharmaceutically-acceptable carriers, and such administration can be carried out in both single and multiple doses.

For purposes of oral administration, tablets containing various excipients such as sodium citrate, calcium carbonate and dicalcium phosphate may be employed along with various disintegrants such as starch, alginic acid and certain complex silicates together with binding agents such as polyvinylpyrollidone, sucrose, gelatin and gum acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials include lactose as well as high molecular weight polyethylene glycols. When aqueous suspensions and/or elixirs are desired for oral administration, the essential active ingredients therein may be combined with various sweetening or flavoring agents, coloring matter or dyes, and if desired, emulsifying and/or suspending agents as well, together with such diluents as water, ethanol, propylene glycol, glycerol and various combinations thereof.

For purposes of parenteral administration, solutions of these antibiotics in sesame or peanut oil or in aqueous propylene glycol may be employed.

The following examples are given to more fully illustrate the invention. It is to be understood that these examples are for illustrative purposes only and that the invention is not meant to be limited to the specific details of the examples.

EXAMPLE I

A sterile aqueous medium having the following composition is prepared:

| Ingredient | Grams/liter |
|---|---|
| Glucose | 10 |
| Starch | 20 |
| Enzymatic digest of casein | 5 |
| Yeast extract | 5 |
| $CaCO_3$ | 1 |
| pH – 7.0 | |

Cells from a slant culture of *M. viridifaciens* ATCC 31146 are transferred to each of a number of 300 ml Erlenmeyer flasks containing 50 ml of this medium and shaken on a rotary shaker for about three to four days at 29°–30° C.

Fermentors containing two liters of the above described sterile medium are seeded with 5% v/v of the grown inoculum. The temperature is maintained at 28° to 36° C. and the broth is stirred at 1700 r.p.m. and aerated at the rate of 0.5 to 1.0 volume of air per volume of broth per minute. After about 60 to 90 hours the broth is filtered and extracted twice with ⅓ to ½ volumes of methyl isobutyl ketone. The combined solvent extract is taken to dryness under vacuum and defatted with heptane. The small amount of Compound 37,504 contained in the mycelial filter cake is removed by stirring for about an hour with sufficient methanol to give a thin slurry. After filtering the methanol extract is concentrated under vacuum to about 1/10 volume and twice extracted with ⅓ to ½ volumes of methyl isobutyl ketone. The methyl isobutyl ketone extract is separated, concentrated to dryness under vacuum and defatted with heptane or petroleum ether.

EXAMPLE II

The fermentation process of Example I is repeated. About 5% v/v of the grown inoculum is used to inoculate a fermentor containing about 2000 gallons of a medium of the following composition:

| Ingredient | Grams/liter |
|---|---|
| Yeast extract | 5 |
| Glucose | 10 |
| Starch | 20 |
| Enzymatic digest of casein | 5 |
| $CaCO_3$ | 2 |
| pH – 7.2 | |

The fermentation is conducted as in Example I with soybean oil added as necessary to control foam. After substantial antibiotic activity is obtained (approximately 90 to 120 hours) the whole fermentation broth is adjusted to pH 7 and extracted with methyl isobutyl ketone by means of a Podbielniak extractor. The solvent extract is concentrated under vacuum to about 5 liters to which are then added three volumes of heptane. The material that separates is collected by filtration and dried overnight under vacuum at 50° C. to yield 92 grams of a dark solid.

A 3 gram portion of the dark solid is dissolved in chloroform and applied to a column 1 inch × 92 cm. of silica gel $PF_{254}$ (E. Merck, Darmstadt, Germany) made up in chloroform. The column is developed under 80 psi with chloroform, chloroform:methanol (98:2% v/v) and chloroform:methanol (95:5% v/v) at a rate of 4 ml per minute. Cuts of 20 ml are collected and assayed by thin layer chromatography. The cuts containing Compound 37,504 are combined and taken to dryness under vacuum. The amorphous yellow powder is treated with activated charcoal (Darco G 60) in chloroform:methanol (1:1 v/v) solution. Evaporation under vacuum yields an amorphous yellow powder which cannot be induced to crystallize. This material is freely soluble in methyl isobutyl ketone, ethanol, methanol, chloroform, dimethylsulfoxide and dimethylformamide; it is insoluble in water, diethyl ether, hexane and heptane.

Antibiotic Compound 37,504 gives on analysis the following average proportions:

| | |
|---|---|
| Carbon | 52.13 |
| Hydrogen | 4.52 |
| Nitrogen | 10.95 |
| Oxygen (by difference) | 32.40 |

Compound 37,504 is optically active, having a rotation of $[\alpha]_D^{25°} = +111°$ ($c = 1\%$ in methanol). Its ultraviolet absorption maxima in methanol occur at 225, 285, 365 and 410 mµ with $E_{1\ cm}^{1\%}$ values of 563, 241, 96 and 35, respectively.

The infrared spectrum of Antibiotic Compound 37,504 is attached. A chloroform solution shows characteristic absorption in the infrared region at the following wavelengths in microns: 2.97, 3.44, 5.75, 5.98, 6.55, 7.10, 7.24, 7.58, 8.00, 8.88, 9.00, 9.10, 9.90 and 10.22.

What is claimed is:

1. Antibiotic Compound 37,504 which is soluble in methyl isobutyl ketone, ethanol, methanol, chloroform, dimethylsulfoxide and dimethyl formamide, and insoluble in water, diethyl ether, hexane and heptane; has an optical rotation of $[\alpha]_D^{25°} = +111°$ at a concentration of 1% in chloroform; absorption maxima in the ultraviolet light region of the spectrum in methanol at 225, 285, 365 and 410 mµ with $E_{1\ cm}^{1\%}$ values of 563, 241, 96 and 35, respectively; average composition by weight of 52.13% carbon, 4.52% hydrogen, 10.95% nitrogen and 32.40% oxygen (by difference); and when dissolved in chloroform exhibits characteristic absorption in the infrared region at the following wavelengths in microns: 2.97, 3.44, 5.75, 5.98, 6.55, 7.10, 7.24, 7.58, 8.00, 8.88, 9.00, 9.10, 9.90 and 10.22.

2. A process for producing Antibiotic Compound 37,504 which comprises cultivating *Micromonospora viridifaciens* sp. nov. Routien, ATCC 31146 at a temperature of 28°–36° C. in an aqueous nutrient medium containing a source of carbohydrate, a source of organic nitrogen and inorganic salts under submerged aerobic conditions until substantial antimicrobial activity is imparted to said medium.

3. A process as in claim 2 wherein said Antibiotic Compound 37,504 is separated from the whole fermentation broth by the following steps:
   a. extractng with methyl isobutyl ketone at pH 4 to 10;
   b. concentrating under vacuum the solvent extract of steps (a) and precipitating Compound 37,504 with 3 volumes of heptane; and
   c. chromatographing on silica gel column developed with chloroform, chloroform:methanol (98:2% v/v) and chloroform:methanol (95:5% v/v).

* * * * *